United States Defensive Publication [19] (H) [11] T979,003

Jamieson [43] Feb. 6, 1979

[54] METHOD FOR PREPARING N-(CARBOXYETHYL-p-AMINOPHENOL

[75] Inventor: Norman C. Jamieson, St. Louis County, Mo.

[73] Assignee: Mallinckrodt, Inc., St. Louis, Mo.

[21] Appl. No.: 877,914

[22] Filed: Feb. 15, 1978

[51] Int. Cl.[2] ..... C07C 51/00

[52] U.S. Cl. ..... 562/452

[57] ABSTRACT

N-(2-carboxyethyl)-p-aminophenol is prepared by reacting p-aminophenol with at least an approximately equimolar proportion of a lower alkyl acrylate in a solvent for the reactants to form an N-(2-carbalkoxyethyl)-p-aminophenol, separating the N-(2-carbalkoxyethyl)-p-aminophenol, hydrolyzing it to form N-(2-carboxyethyl)-p-aminophenol and isolating the N-(2-carboxyethyl)-p-aminophenol substantially free of impurities.

7 Claims, No Sheets Drawing,

8 Pages Specification

The file of this unexamined application may be inspected and copies thereof may be purchased (849 O.G. 1221, Apr. 9, 1968).